US00PP17595P3

(12) United States Plant Patent

Yomo et al.

(10) Patent No.: US PP17,595 P3
(45) Date of Patent: Apr. 17, 2007

(54) *VERBENA* PLANT NAMED 'SUNTAPILABU'

(50) Latin Name: *Verbena hybrida*
Varietal Denomination: Suntapilabu

(75) Inventors: Yasunori Yomo, Kawasaki (JP); Naoto Takamura, Omihachiman (JP)

(73) Assignee: Suntory Flowers Limited, Tokyo (JP)

( * ) Notice: Subject to any disclaimer, the term of this patent is extended or adjusted under 35 U.S.C. 154(b) by 130 days.

(21) Appl. No.: 10/814,618

(22) Filed: Mar. 30, 2004

(65) Prior Publication Data

US 2005/0223456 P1 Oct. 6, 2005

(51) Int. Cl.
*A01H 5/00* (2006.01)

(52) U.S. Cl. ..... Plt./308
(58) Field of Classification Search ..... Plt./308
See application file for complete search history.

(56) References Cited

U.S. PATENT DOCUMENTS

PP9,121 P 4/1995 Tachibana et al.
PP9,411 P 12/1995 Tachibana et al.

FOREIGN PATENT DOCUMENTS

JP PBR 4432 3/1995
JP PBR 4434 3/1995

OTHER PUBLICATIONS

Flower & Green Catalog 2004, Suntory Flowers, Ltd., (4 pp), Published 2003, 2 with brief English explanation and partial translation of page 14.

The 2004 Suntory Collection, Jackson & Perkins Wholesale, Inc., (3 pp), Published 2003, with brief English translation of pages 5 and 13.

Explanation of Publications of Japanese PBR Registrations and family documents therein.

Pineae Peak Performers featuring the 2004 Suntory Collection, Pineae Greenhoses, Inc., (3 pp), Published 2003 with brief English translation of page 8.

Suntory Collection 2004, Moerheim New Plant bv, (4 pp), Published 2003 with brief English translation of pages 63 and 65.

Colour Wave Collection 2003–04, Ramm Botanicals Pty Ltd., (3 pp), Published 2002.

*Primary Examiner*—Anne Marie Grunberg
*Assistant Examiner*—Georgia Helmer
(74) *Attorney, Agent, or Firm*—Christie, Parker & Hale, LLP

(57) ABSTRACT

Disclosed herein is a new and distinct variety of *Verbena* plant having a decumbent and compact growth habit. The *Verbena* plant has abundant branching, the whole plant remaining in bloom for a considerable period of time. The flowers are formed in profusion in a spike and the petals display a strong purple color. The blooming period is from April to November, and the flowering duration is long. The plant exhibits high tolerance to heat, high resistance to rain, pests and disease, particularly powdery mildew.

2 Drawing Sheets

Botanical classification: *Verbena hybrida.*
Varietal denomination: 'Suntapilabu'.

BACKGROUND OF THE VARIETY

The present invention relates to a new variety of *Verbena* plant, which originated from the crossing of a *Verbena* hybrid variety called 'T86-99-2' (unpatented) as the female parent and 'T85-99-2' (unpatented) as the male parent.

The *verbena* is a very popular plant and is used for flower bedding and potting in the summer season. There are only a few varieties of *Verbena* plants which have a spreading growth habit, abundant branching, a large number of flowers in clusters and a high resistance to rain, heat, cold, and disease. Accordingly, this invention was aimed at obtaining a new variety having a decumbent and compact growth habit, many branches, a large number of flowers in clusters, high tolerance to heat, rain, drought and cold, and resistance to disease and pests combined with strong purple petal coloration.

The female parent 'T86-99-2' used in the crossing that produced 'Suntapilabu' is a strain of our breeding lines, having a decumbent growth habit. The peduncle is longer, and the spike diameter and the floret diameter are smaller, than those of 'Suntapilabu'. The petal color of 'T86-99-2' is purplish white, while that of 'Suntapilabu' is purple.

The male parent 'T85-99-2' used in the crossing that produced 'Suntapilabu' is a strain of our breeding lines, having a decumbent growth habit. The stem length is longer, and the plant height is lower, than that of 'Suntapilabu'. The petal color of 'T85-99-2' is light blue, which is lighter than that of 'Suntapilabu' (near R.H.S. N81B).

In March 1999, crossing of 'T86-99-2' as the female parent and 'T85-99-2' as the male parent was conducted at Yokaichi-shi, Shiga-ken, Japan. In June 1999, seedlings were obtained from that crossing. These seedlings were grown in pots in glasshouses and were evaluated. Five seedlings were selected in view of their growth habit and flower color in October 2000. Those seedlings were propagated by cutting and a trial was carried out by flower potting and bedding from May to October 2001. The botanical characteristics of those plants were then examined, using similar varieties 'Sunmaref TP-L' (U.S. Plant Pat. No. 9,121) and 'Sunmaref TP-V' (U.S. Plant Pat. No. 9,411) for comparison. One plant was selected and determined to be distinguishable from any other *Verbena* variety, whose existence is known to us, and to be uniform and stable in its characteristics. The new variety of *Verbena* plant was named 'Suntapilabu'.

In the following description, the color-coding is in accordance with The Horticultural Colour Chart of The Royal Horticultural Society, London, England (R.H.S.).

SUMMARY OF THE VARIETY

This new variety is unlike any commercially available *Verbena* known to us as evidenced by the following unique combination of characteristics.

1. Decumbent and compact growth habit with abundant branching.
2. Plentiful number of flowers in a spike having a great profusion of blooms with the entire plant remaining in bloom for a considerable period of time.
3. Long flowering duration.
4. The petal color is strong purple (near R.H.S. N81B).
5. The plant has a high resistance to rain, heat, disease and pests.

The new variety 'Suntapilabu' differs from the similar variety 'Sunmaref TP-L' in the following points.

1. The spreading area of 'Suntapilabu' is smaller than that of 'Sunmaref TP-L'.
2. The flower color of 'Suntapilabu' is strong purple (near R.H.S. N81B), while that of 'Sunmaref TP-L' is brilliant purple (near R.H.S. N88C).
3. The peduncle length of 'Suntapilabu' is shorter than that of 'Sunmaref TP-L'.
4. The flower fragrance of 'Suntapilabu' is present, while that of 'Sunmaref TP-L' is absent.

The new variety 'Suntapilabu' differs from the similar variety 'Sunmaref TP-V' in the following points.

1. The spreading area of 'Suntapilabu' is smaller than that of 'Sunmaref TP-V'.
2. The leaf of 'Suntapilabu' is smaller than that of 'Sunmaref TP-L'.
3. The spike length of 'Suntapilabu' is shorter than that of 'Sunmaref TP-V'.
4. The flower color of 'Suntapilabu' is strong purple (near R.H.S. N81B), while that of 'Sunmaref TP-V' is vivid purple (near R.H.S. N81A).

The new variety of *Verbena* Plant 'Suntapilabu' was asexually reproduced by the use of cuttings at Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPHS

The depicted plants had been reproduced by the use of cuttings and were photographed during April 2003 while growing outdoors in 24 cm pots at an age of approximately 6 months at Yokaichi-shi, Shiga-ken, Japan.

DESCRIPTION OF THE VARIETY

Figure 1:
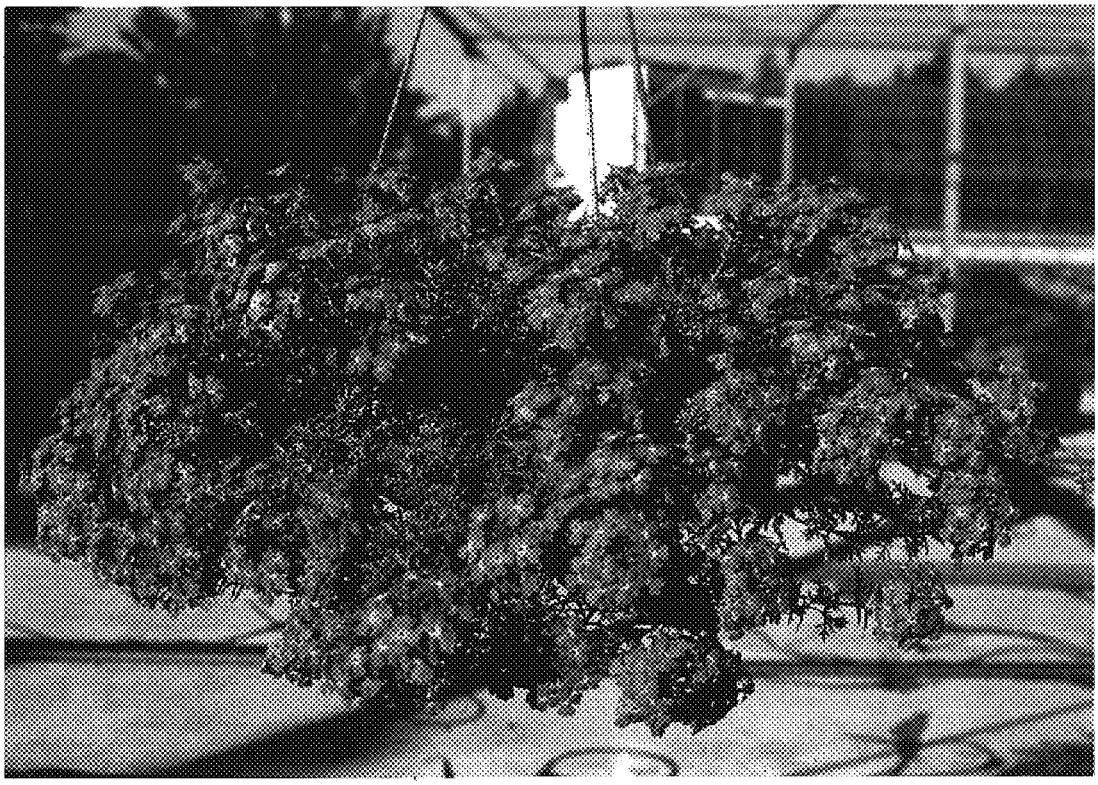
FIG. 1 illustrates a typical plant of the new variety of *Verbena* plant 'Suntapilabu' while growing in a pot.
Figure 2:
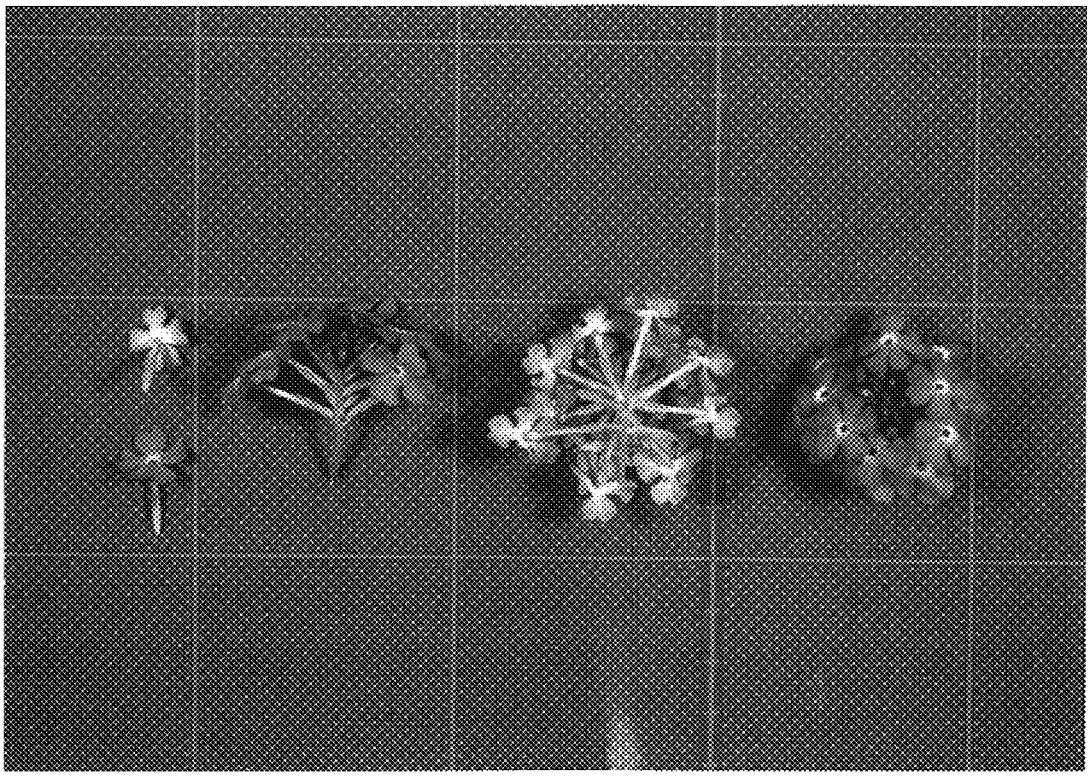
FIG. 2 illustrates a close view of typical blossoms of the new variety of *Verbena* plant 'Suntapilabu'.

The botanical characteristics of the new and distinct variety of *Verbena* plant named 'Suntapilabu' are as follows when observed during October at Yokaichi-shi, Shiga-ken, Japan, at an age of approximately 6 months.

Plant:
- *Growth habit.*—Decumbent.
- *Plant width.*—Approximately 62 cm.
- *Plant height.*—Approximately 17 cm.

Stem:
- *Diameter.*—Approximately 2.0 mm.
- *Anthocyanin pigmentation.*—Present.
- *Pubescence.*—Sparse.
- *Prickles.*—Absent.
- *Branching.*—Abundant.
- *Subterranean stem.*—Absent.
- *Length of internode.*—Approximately 3.0 cm.

Leaf:
- *Phyllotaxis.*—Opposite.
- *Shape of blade.*—Hastate.
- *Apex shape.*—Obtuse.
- *Base shape.*—Truncate.
- *Margin.*—Pinnatisect.
- *Length.*—Approximately 2.0 cm.
- *Width.*—Approximately 2.0 cm.
- *Color.*—Adaxial side: Near R.H.S. 137A (dark olive green); Abaxial side: Near R.H.S. 137C.
- *Pubescence.*—Normal.
- *Petiole.*—Absent.

Flower:
- *Shape of cluster.*—Obconical.
- *Spike length.*—Approximately 2.5 cm.
- *Spike diameter.*—Approximately 5.5 cm.
- *Facing direction.*—Upward.
- *Floret diameter.*—Approximately 1.7 cm.
- *Floret length.*—Approximately 1.3 cm.
- *Color of petal.*—Upper surface: Near R.H.S. N81B (strong purple); Lower surface: Near R.H.S. N81D.
- *Eye color.*—Near R.H.S. 155B.
- *Variegation.*—Absent.
- *Petal apex.*—Emarginate.
- *Petal width.*—Approximately 8.0 mm.
- *Petal length (from the throat).*—Approximately 6.6 mm.
- *Number of petals.*—Generally 5.
- *Calyx length.*—Approximately 0.9 cm.
- *Calyx shape.*—Tubular. Sepals have an acute apex and are fused at the base.
- *Reproductive organs.*—1 pistil and 4 stamens.
- *Pistil shape.*—Bifid.
- *Anther color.*—Near R.H.S. 1B (yellow green).
- *Filament color.*—Near R.H.S. 1B (yellow green).
- *Pollen.*—Present in a moderate quantity.
- *Stigma color.*—Near R.H.S. 4D (pale yellow green).
- *Style color.*—Near R.H.S. 144B (strong yellow green).
- *Ovaries.*—Commonly four in number.
- *Peduncle diameter.*—Approximately 2.0 mm.
- *Peduncle length.*—Approximately 3.0 cm.
- *Peduncle color.*—Near R.H.S. 137C (moderate yellow green).
- *Number of flowers.*—Approximately 25 florets per spike.
- *Flower fragrance.*—Present.
- *Flowering period.*—April to November in the southern Kanto area, Japan. The plant shape does not change throughout this period. A typical flower commonly lasts 5 to 7 days on the plant when experiencing a temperature of approximately 20° C.

*Fruit and seed.*—Fruit and seed production has not been observed.

Physiological and ecological characteristics:

*Resistance to rain.*—High.

*Winter hardiness.*—USDA Hardiness Zone 4–9 (Grown as perennial).

*Heat tolerance.*—The plant grows well at temperatures up to at least 35° C.

*Disease and pest resistance.*—Resistant to powdery mildew. No serious damage by pathogen and pests common to *Verbena* has been observed.

It is claimed:

1. A new and distinct variety of *Verbena* plant named 'Suntapilabu', substantially as herein illustrated and described.

* * * * *